United States Patent
Warner et al.

(10) Patent No.: US 10,610,318 B2
(45) Date of Patent: Apr. 7, 2020

(54) AUGMENTED REALITY CATHETER INTERFACE

(71) Applicant: General Electric Company, Schenectady, NY (US)

(72) Inventors: Adrian F. Warner, Wauwatosa, WI (US); Rodger F. Schmit, Wauwatosa, WI (US); Daniel R. Schneidewend, Wauwatosa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 591 days.

(21) Appl. No.: 15/218,640

(22) Filed: Jul. 25, 2016

(65) Prior Publication Data

US 2018/0021099 A1   Jan. 25, 2018

(51) Int. Cl.
*A61B 34/00*   (2016.01)
*G06F 3/01*   (2006.01)
(Continued)

(52) U.S. Cl.
CPC .............. *A61B 34/76* (2016.02); *G06F 3/016* (2013.01); *A61B 2034/741* (2016.02);
(Continued)

(58) Field of Classification Search
CPC ... A61B 2034/741; A61B 34/74; A61B 34/70; A61B 34/00; A61B 34/25; A61B 2034/254; A61B 2034/256; A61B 2034/258; A61B 90/00; A61B 90/06; A61B 2090/064; A61B 2090/065; A61B 34/76; A61M 2205/582; A61M 25/0136; A61M 25/0116; A61M 2205/58;
(Continued)

(56) References Cited

U.S. PATENT DOCUMENTS

| 7,963,925 B1 | 6/2011 | Schecter |
| 8,390,438 B2 | 3/2013 | Olson et al. |

(Continued)

FOREIGN PATENT DOCUMENTS

| EP | 2777585 | 9/2014 |
| WO | 2006120666 | 11/2006 |

OTHER PUBLICATIONS

Extended European Search Report and Opinion issued in connection with corresponding EP Application No. 17179988.5 dated Dec. 15, 2017.

*Primary Examiner* — Jason E Flick
(74) *Attorney, Agent, or Firm* — Boyle Fredrickson, S.C.

(57) ABSTRACT

In the present invention, a haptic feedback module for use with a medical computer system employed in non-robotic interventional medical procedure is provided for placement on a catheter control handle. The haptic feedback module includes transducers that are operably connected to the computer system in order to enable the feedback module to provide haptic feedback to a user in response to sensor data and other information supplied to the computer system. The haptic feedback module is formed as a separate component that is releasably attachable to the catheter control handle to enable a user to receive the haptic feedback while retaining control of the catheter control handle being utilized in the interventional medical procedure.

15 Claims, 3 Drawing Sheets

(51) Int. Cl.
    *A61M 25/01*      (2006.01)
    *A61B 90/00*      (2016.01)
(52) U.S. Cl.
    CPC .... *A61B 2090/065* (2016.02); *A61M 25/0116* (2013.01); *A61M 25/0136* (2013.01); *A61M 2205/582* (2013.01)
(58) Field of Classification Search
    CPC ............ A61M 2205/586; A61M 25/01; A61M 25/0105; A61M 25/0133; G06F 3/016; G06F 3/00; G06F 3/01; G06F 3/014
    USPC ...................................................... 604/95.01
    See application file for complete search history.

(56) References Cited

U.S. PATENT DOCUMENTS

| | | | |
|---|---|---|---|
| 8,663,122 B2 | 3/2014 | Schecter | |
| 8,942,828 B1 | 1/2015 | Schecter | |
| 2005/0209524 A1 | 9/2005 | Donaldson et al. | |
| 2013/0321262 A1* | 12/2013 | Schecter | G06F 3/041 345/156 |
| 2017/0196479 A1* | 7/2017 | Liu | G01K 13/002 |

* cited by examiner

AUGMENTED REALITY CATHETER INTERFACE

BACKGROUND OF INVENTION

The invention relates generally to catheters utilized in interventional medical procedures, and more particularly to a feedback system for a catheter that provides non-visual indications or cues to an individual utilizing the catheter.

Catheters are used in an increasing number of interventional medical procedures to evaluate various conditions of the patient with which the catheter is utilized. In performing the procedure with a catheter, with most catheter designs the physician holds a handle for the catheter from which extends a shaft that is inserted into the body of the patient. The physician holds the catheter handle with one hand while operating controls on the handle with the other hand to move the shaft and catheter tip into the desired location to obtain information on and/or images of the tissue being investigated and/or treated.

Due to the length of the shaft extending from the handle of the catheter, direct tactile feedback from the catheter tip and shaft is limited at the handle and thus the physician through the shaft. This, in turn, limits the ability of the physician to sense the location of the catheter through the tactile feedback from the catheter, i.e., the forces exerted on the catheter tip and shaft by the tissue contacted by the tip and shaft, thereby limiting the information provided to the physician during the procedure. Additionally, other important catheter state information, such as the occurrence of pacing or ablation on that catheter, produce no mechanical feedback to the catheter handle.

In certain prior art solutions to this issue, various imaging/recording systems designed to be connected to the catheter to have been developed that are capable of displaying the information regarding the forces exerted on the catheter tip and shaft on a display in conjunction with the images of the tissue being investigated and/or treated. However, in order to receive this information, the physician must necessarily look at the display in the location where the information is illustrated. This, in turn, requires that the physician look elsewhere than at the images representing the tissue being investigated on the display to view the information. However, these secondary representations on the display can be distracting and are often hard to gauge and require the physician to interpret the information represented, as in a charts, while performing the procedure, all of which can temporarily shift the physician's focus, which is undesirable.

Other alternative solutions to provide the feedback on the forces exerted on the catheter tip and/or shaft include audible sounds and/or warnings, but these provide little, if any information to the physician on the actual forces acting on the catheter tip and/or shaft.

As an alternative to visual and audible feedback systems associated with the recording/mapping/imaging systems to which the catheter is connected, one additional prior art feedback alternative that has been developed is the use of robotic interventional systems that includes haptic feedback provided to the physician. One such system is disclosed in U.S. Pat. No. 8,390,438, entitled Robotic Catheter System Including Haptic Feedback, which is expressly incorporated herein by reference for all purposes. In this system, a robotic catheter system includes an input control system designed to control the operation of a robotic catheter manipulator assembly such that the physician can remotely perform an interventional procedure with the robotic catheter manipulator assembly by utilizing the input control system. The robotic catheter system also includes a haptic feedback system located on the input control system. The haptic feedback system is disposed in conjunction with a user interface device that forms a part of the input control system. The haptic feedback system provides mechanical resistance and other types of feedback to the user through the user interface device corresponding to the resistance and other types of information provided by the catheter and other sources, such as sensors disposed on the catheter.

In addition to the disclosed robotic catheter system, the '438 patent additionally discloses that the haptic feedback system can be disposed directly within a handle for the catheter, in which cases the user input system is omitted. The feedback from the haptic feedback system in this prior art system is sent directly back to the catheter handle to be received by the physician holding the catheter handle in order to provide the information contained within the feedback to the physician.

The '438 patent also discloses an embodiment where the haptic feedback system is configured with the user input system in the form of a glove that is worn by the user and employed with feedback sensors in a three-dimensional imaging system or liquid tank. The sensors on the glove are provided with the feedback from the catheter that is transmitted through the glove to the wearer for use in the performance of the procedure.

While the prior art solution provided in the '438 patent enables haptic feedback to be transmitted directly back to the physician via the user input system, whether a remote system or incorporated into the catheter handle, in either embodiment the utilization of the feedback system requires either the use of a robot and the remote user input system or a catheter handle that is constructed with the haptic feedback system and all of the accompanying feedback devices within the handle. Thus, the haptic feedback system of the '438 patent requires significant increases in equipment investment/cost and complexity in the catheter system utilized to perform the procedure in order to provide the feedback to the physician.

Accordingly, it is desirable to develop a system and method for a haptic feedback system for use with a manually-operated catheter employed in medical interventional procedures that is capable of providing effective haptic feedback to the user of the catheter without significant alterations or changes to existing catheter configurations. It is also desirable that this system allow the use of haptic feedback with wide array of currently available off the shelf catheters so as to allow the physician to choose the most appropriate catheter for the application. Finally, it is desirable that the haptic feedback system allow tactical sensation of more general system events not related to catheter pressure or location (such as the presence of pacing or ablation signals)

BRIEF DESCRIPTION OF THE INVENTION

There is a need or desire for a haptic feedback system for a manually operated catheter that enables the physician/user to operate a catheter in a conventional manner while also receiving haptic feedback from the feedback system. The feedback system includes a haptic feedback module/interface that can be positioned on the hand of the user or on a catheter control handle in a manner that does not obstruct the ability of the physician to hold and operate the controls on the handle while providing the haptic feedback to the user. The above-mentioned drawbacks and needs are addressed by the embodiments described herein in the following description. The feedback module provides physical feedback in the form of haptic (pressure, direction, guidance) and temperature (ablation, danger, direction combined with force) such that the physician can receive implicit direction/guidance from the computer system. Through this feedback, the user is in constant touch with the procedure and can interpret the tactile feedback to provide additional guidance either in navigation, tissue contact, or as physical representation or direction for the completion of the procedural steps in the procedure being performed. The feedback system is designed for non-robotic use to provide the user heightened or additional feel of the catheter either in the form of feedback (as in resistance magnification) or in the form of guidance in terms of touch, as well as additional feedback/sensing signals including heat and cold, and the presence pacing and ablation signals among others.

According to one exemplary non-limiting aspect of the invention, a haptic feedback system and module for use with a medical computer system employed in non-robotic interventional medical procedure is provided for placement on a catheter control handle. The haptic feedback module includes transducers that are operably connected to the computer system in order to enable the feedback module to provide haptic feedback to a user in response to sensor data and other information supplied to the computer system. The haptic feedback module is formed as a separate component that is releasably attachable to the catheter control handle to enable a user to receive the haptic feedback while retaining control of the catheter control handle being utilized in the interventional medical procedure.

According to one exemplary non-limiting embodiment of the invention, the haptic feedback module is formed with a housing that is releasably positionable on a control handle for the catheter. The housing includes a central processor, a transceiver for communication with a control system for the catheter, such as a recording/mapping system, and a number of transducers disposed within the housing and capable of being activated in order to produce selected types of haptic feedback to be conveyed from the housing to the user of the catheter.

According to another exemplary non-limiting embodiment of the invention, the housing for the haptic feedback module is formed to be placed directly on a hand of the user of the catheter, such as a glove. The housing in this exemplary non-limiting embodiment also includes a central processor, a transceiver and a number of transducers or similar devices for the production of haptic feedback for transmission to the user of the system through the housing.

According to another aspect of one exemplary non-limiting embodiment of the invention, a haptic feedback module for a catheter control handle utilized in a non-robotic interventional medical procedure includes a housing configured to be releasably secured to a control handle and a number of transducers disposed at least partially within the housing, wherein the number of transducers are operable to provide haptic feedback in response to signals from a computer system.

According to still a further aspect of one exemplary non-limiting embodiment of the invention, catheter control handle includes a housing, a shaft extending outwardly from the housing, the shaft terminating in a tip including at least one sensor and optionally an electrode, a conductor extending outwardly from the housing and configured to be connected to an computer system to supply sensor data thereto, a control device disposed on the housing and connected to the shaft to control the shaft and a haptic feedback module releasably disposed on the housing, the haptic feedback module configured to be connected to a computer system to control the operation of the haptic feedback module in response to signals from the computer system relating to sensor data, steps in a non-robotic medical interventional procedure, interface actions or sensor warnings.

According to still a further aspect of one exemplary non-limiting embodiment of the invention, a method of providing haptic feedback to a user of a manually-operated catheter control handle during a non-robotic interventional medical procedure includes the steps of providing a catheter control handle including a housing, a shaft extending outwardly from the housing and terminating in a tip including at least one sensor and optionally an electrode, a conductor extending outwardly from the housing and connected to an computer system to supply sensor data thereto, a control device disposed on the housing and connected to the shaft to control the shaft and a haptic feedback module releasably disposed on the housing, the haptic feedback module including a number of transducers connected to the computer system to control the operation of the transducers, securing the haptic feedback module to the housing, receiving sensor data in the computer system from the at least one sensor and operating the transducers in response to the sensor data.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
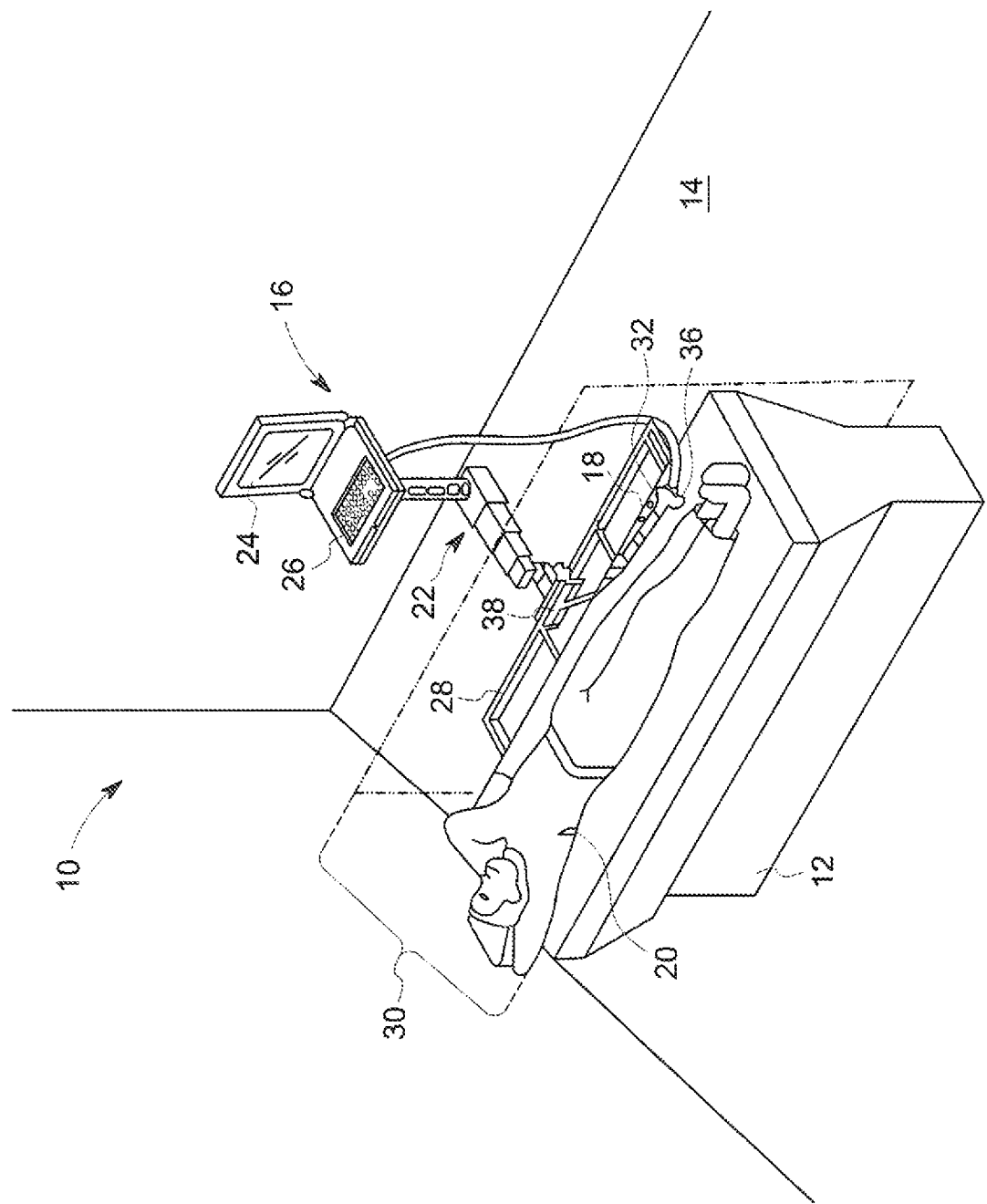
FIG. 1 is a schematic representation of an interventional mapping/recording/imaging system including a catheter control handle according to one exemplary non-limiting embodiment of the invention.

Referring to FIG. 1, in the illustrated exemplary non-limiting embodiment a patient care facility 10, such as an interventional lab/operating room 14, includes a patient bed 12, a computer system, such as a medical mapping/imaging/recording device 16, and a catheter 18. Patient bed 12 is configured to support a patient 20 in the interventional lab/operating room 14 so that medical imaging/recording device 16 may obtain internal medical images of patient 20 using the catheter 18. In various exemplary non-limiting embodiments, patient bed 12 may be a bed of any suitable design that is capable of supporting the patient 20 while performing the interventional procedure with the system 16 and the catheter 18.

The medical mapping/imaging/recording device or system 16 can be any suitable system for obtaining, recording, mapping and/or manipulating images of the selected tissue within the patient 20 via the catheter 18 for investigative and/or treatment purposes, such as US Patent Application Publication No. US2005/0209524A1, entitled System And Method For Receiving And Storing Information Pertaining To A Patient, which is expressly incorporated herein by reference in its entirety for all purposes. In the illustrated exemplary non-limiting embodiment of FIG. 1 the system 16 may include a mounting structure 22 connected to the table 12 that supports a display screen 24 on which the physician can view the images provided by the catheter 18. The system 16 can also include an interface 26 operably connected to the display 24 and which can be utilized by a physician directly interact with the system 16, such as to illustrate selected images on the display and/or to obtain measurements on the images illustrated on the display 24. The system 16 can additionally be configured in a known manner, such as by using a wired or wireless connection, to be operably connected to a computer network (not shown) located within the patient care facility 10 in order to transmit the data and images obtained by the system 16 to and via the network to a remote location, as desired.

In the illustrated exemplary non-limiting embodiment, the mounting structure 22 is configured to support the display 24 and is coupled to bed 12 via a rail 28 in an area external to a sterile zone or field 30 encompassing bed 12. In another exemplary non-limiting embodiment, mounting structure 22 may be coupled to bed 12 via means other than a rail. Mounting structure 22 is capable of positioning display 24 in a variety of locations as desired by a clinician for various reasons such as for best viewing or so as to not be obstructing any procedure performed on patient 20. In other exemplary non-limiting embodiments, mounting structure 22 may be a cart that is not directly coupled to bed 12.

Figure 2:
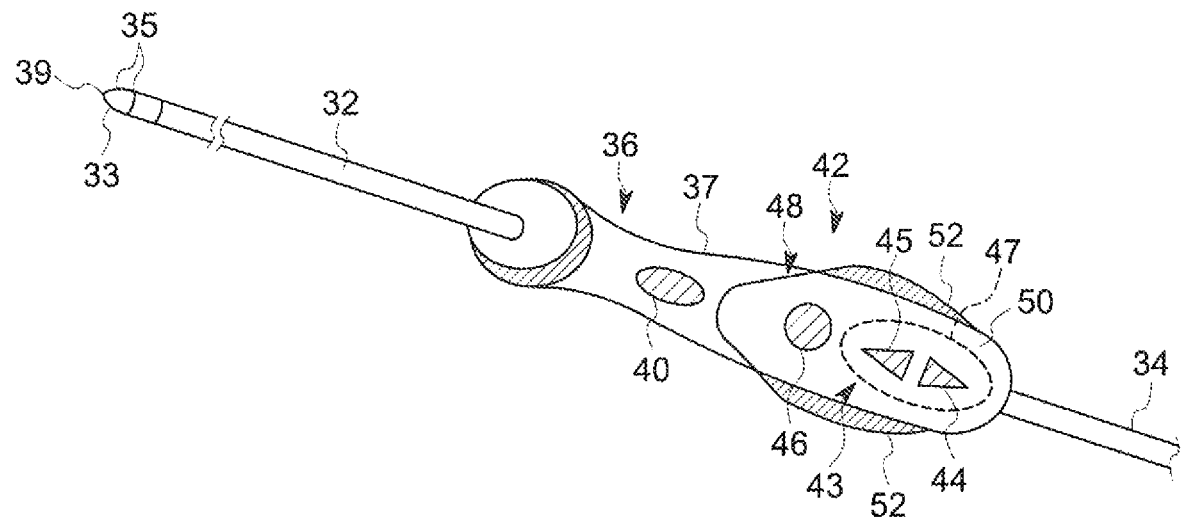
FIG. 2 is an isometric view of a catheter control handle including a haptic feedback interface module according to an exemplary non-limiting embodiment of the invention.

Looking now at FIG. 2, catheter 18 can be any suitable type of tool and/or catheter utilized to perform an interventional procedure on the patient 20, such as a catheter 18 useful for a variety of procedures including, without limitation, spiral catheters, ablation catheters, mapping catheters, balloon catheters, needle/dilator tools, cutting tools, cauterizing tools, and/or gripping tools. The catheter 18 is configured to be inserted into patient 20 to cooperate with medical mapping/imaging system 16 and obtain sensor and medical imaging data for representation on the display 24 and/or to treat the tissue within the patient 20 contacted by the catheter 18. In the exemplary non-limiting illustrated embodiment of FIG. 2, the catheter 18 includes a control handle 36 through which extends a shaft 32 having a tip 33 for insertion into the patient 20. The shaft 32 and/or the tip 33 include a number of sensors 35 to sense various attributes of the tissue in contact with the catheter 18, e.g., the temperature, force and torque applied against the catheter tip 33 and shaft 32. The tip 33 may also include one or more electrodes 39 or other tissue-affecting members to apply heat, cold or other tissue-affecting structures or energy to the tissue surrounding the catheter tip 33.

The handle 36 is operatively connected opposite the shaft 32 to a conductor 34 that connects the handle 32 to the mapping/imaging/recording system 36 and extends through shaft 32. The conductor 34 enables the various sensor and image signals obtained by the shaft 32 and/or tip 33 to be transmitted along the conductor 34 though the catheter 18 to the mapping/imaging system 16 for utilization and processing by the system 16. Additionally, signals from the system 16 can be transmitted along the conductor 34 to the tip 33, such as for the treatment of the tissue being contacted by the shaft 32/tip 33.

The control handle 36 includes a housing 37 configured to allow gripping of the catheter 18 by a user. The control handle 36 may be manipulated by a user/physician to guide the shaft 32 and tip 33 to a desired location within the patient 20 to obtain and retrieve data from within patient 20, such as data from sensors 35 for use by the system 16. In one exemplary non-limiting embodiment, the control handle 36 includes a control device 40 that enables the user/physician to manipulate operate the shaft 32 and/or tip 33 within the patient 20 to move the shaft 32 and/or tip 33 into the desired position(s) within the patient 20 to obtain the desired sensor data or to treat the selected tissue, such as by using electrodes 37. The control device 40 can have any suitable or desired configuration to enable the physician to remotely manipulate the position of the shaft 32 and/or tip 33 within the patient 20 as desired. In exemplary non-limiting embodiments where the catheter 18 is utilized to treat the tissue within the patient being contacted by the shaft 32 and/or tip 33, the control device 40 can include control elements (not shown) for the manipulation of the shaft 32 and/or tip 33 and for the operation of the treatment elements or electrodes 39 disposed on the shaft 32 and/or tip 33, e.g., as in the case where the catheter 18 is an ablation catheter.

Figure 3:
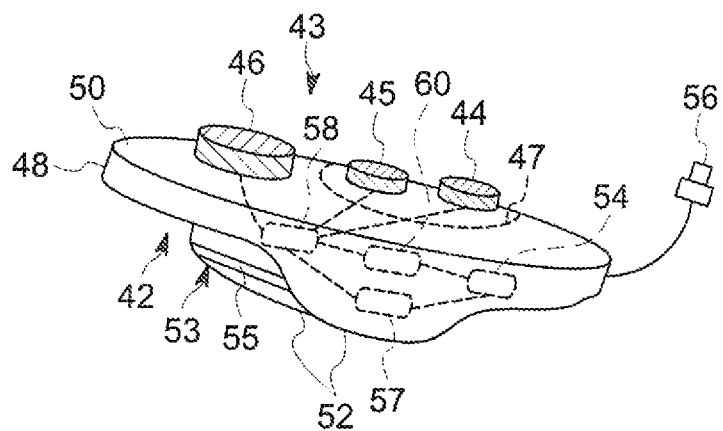
FIG. 3 is an isometric view of the haptic feedback interface module according to another exemplary non-limiting embodiment of the invention.

Referring now to FIGS. 2 and 3, the control handle 36 additionally includes a haptic feedback module 42 disposed thereon. The haptic feedback module 42 is designed for exclusive use with a non-robotic system and is operatively connected to the mapping/imaging/recording system 16, such as via a suitable wired or wireless connection. In the illustrated exemplary non-limiting embodiment of FIGS. 2 and 3, the haptic feedback module 42 can include a housing 48 that is separate from the housing 37 of the control handle 36. The housing 48 is formed of any suitable material, such as of a material that is the same as or similar to that used to form the control handle 36, and has an upper portion that conforms in shape to the shape of the control handle 36. A pair of lower portions 52 extend downwardly from the upper portion on opposite sides of the upper portion 50 and are configured to engage and hold the housing 48 on the control handle 36 in a secure and stable manner. To accomplish this, the lower portions 52 include an engagement structure 53 thereon, such as a rib 55 that is releasably engageable within a complementary groove (not shown) formed in the catheter control handle 36, that operates to engage the housing 48 with the control handle 36 in a suitable and releasable manner, such as by frictionally engaging the control handle 36. In an alternative embodiment, the module 42 can be formed to encircle the handle 36, also providing a secure engagement of the module 42 to the handle 36.

As the housing 48 of the module 42 in the illustrated exemplary non-limiting embodiment is not directly connected to the conductor 34 within the control handle 36, the housing 48 includes a wireless transceiver 54 capable of communicating with the system 16, such as by using near field communications (NFC) technology, Bluetooth® or WiFi signals in order to receive the feedback provided by the system 16 from the catheter 18 to be relayed from the system 16 to the physician via haptic feedback module 42. In an alternative exemplary non-limiting embodiment, the housing 48 can include a separate, and optionally separable, plug-in cable 56, such as a USB or Ethernet compatible cable, that extends outwardly from the housing 48 and is connectable within a suitable port (not shown) disposed on the control handle 36, to connect the module 42 with the conductor 34, or on the system 16. Further, the housing 48 can include a suitable power source 57 capable of operating the haptic feedback module 42, optionally connected with an associated power switch (not shown) for the selective activation of the module 42 when desired. The power source 57 can be replaceable or rechargeable, or can be omitted entirely with the power supplied to the haptic feedback module 42 coming through the plug-in cable 56 extending from the housing 48. Additionally, the housing 48 may include a processing unit 58 for directing the feedback signals supplied via the control elements 43 and electronic storage media 60 operably connected to the processing unit 58 capable of storing various information concerning the operation of the haptic feedback module 42. Further, in order to avoid sterility issues with regard to the use of the module 42, in other exemplary non-limiting embodiments the module 42 can be disposable after use.

The haptic feedback interface module 42 also includes a number of transducers 44, 45, 46 disposed on and/or within the housing 48. The transducers 44-46 are each connected to the processing unit 58 and are operable to provide oscillations or vibrations to the housing 48 that are felt by the user to provide the haptic feedback to the user. The transducers 44-46 can be positioned in any configuration on the housing 48 and can be operated to provide the haptic feedback in any suitable manner. In one exemplary non-limiting embodiment, the transducers 44-46 can be operated via the processing unit 58 together, or can be positioned and/or operated separately in the form of feedback zones 47 formed on certain specified areas of the housing 48. In other exemplary non-limiting embodiments, additional transducers in the form of heating or cooling elements or temperature-variable devices (not shown) can be similarly incorporated on or within the housing 48 to provide haptic feedback to the user regarding the temperatures of the tissue being treated, such as during an ablation procedure.

The plurality of transducers 44-46 individually as well as those present in respective feedback zones 47 can be controlled via the processing unit 58 using feedback patterns or sequences pre-programmed into and stored in the electronic storage media 60. In an exemplary non-limiting embodiment, depending on the type of feedback to be provided to the user based on the information from sensors 35 on the catheter 18 that is received by the processing unit 58 via the system 16, such as feedback indicative of a force, torque or temperature determined by the sensors 35, or a warning relating to an aspect of the current operation of the catheter 18, among others, the processing unit 58 can operate one or more of the transducers 44-46 or a zone 47 of transducers 44-46 in a pattern or sequence to provide the haptic feedback to the user indicative of the type of information to be relayed to the user. For example, when haptic feedback indicative of a force exerted by surrounding tissue on the catheter tip 33 is to be relayed to the user, the processing unit 58 can access the storage media 60 to locate the associated pattern of activation of the transducers 44-46 to be utilized as the haptic feedback to relay the information regarding the force exerted on the tip 33. The processing unit 58 can then use the pre-programmed pattern or sequence to operate one or more of the transducers 44-46 to provide the appropriate haptic feedback to the user contacting the housing 48 and the transducers 44-46. The operation of the transducers 44-46 is optionally done in conjunction with the presentation of the sensor data, warnings or procedure information on the display 24 to provide redundant information sources during the procedure being performed by the physician.

The feedback patterns or sequences for operation of the transducers 44-46 or zones 47 and/or the frequency of operation for each of the transducers 44-46 or zones 47 in the pattern for the various types of haptic feedback to be provided, e.g., mechanical, vibrational, thermal, etc., can be pre-programmed, and optionally altered by the user, and stored locally in the storage media 60 to be accessed by the processing unit 58 in response to information provided by the system 16, such as received from the sensors 35 on the catheter 18. In an alternative exemplary non-limiting embodiment, the patterns or sequences of activation of the transducers 44-46 and/or zones 47 for the various types of haptic feedback can be retained in the system 16 and relayed to the processing unit 58 along the wired or wireless connection between the system 16 and the module 42.

In either configuration, the patterns or sequences of operation of the transducers 44-46 or zones 47 can be initiated relative to data from the catheter 18, as a result or confirmation of various steps in the particular procedure being performed. For example, the transducers may fire once per pacing train to provide feedback on the occurrence and timing of such, or the transducers may increase in vibration intensity as esophageal temperature increases during ablations to provide a progressive warning of potential danger, or can be triggered from suitable computer algorithms within the system 16 relative to warning or feedback sequences based on data from the sensors 35. In this manner, closed loop control of the haptic feedback module 42 can be modified by the computer/system 16 relative to user instruction, or relative to programmed sequences or circumstances relating to the data sensed by the catheter 18 relative to the procedure being performed.

In operation, the haptic feedback module 42 provides implicit feedback to the user to translate and convey a series of user sequences, or circumstances to improve overall situational awareness of situations evolving, or danger trigger points to reinforce other available informational sources within the procedure. For example, rather than having to look at one particular area of the display 24 for a graphic representing pressure, the haptic feedback module 42 can impart via the transducers 44-46 the feeling of the tip 33 striking or contacting the wall of the heart in the case of sensed force via sensors 35. In another exemplary non-limiting embodiment, temperature differences can be applied to the user via appropriate transducers 44-46 or temperature-variable elements on the module 42 to indicate the final stages of an RF ablation procedure using heat or of a cryogenic freezing procedure using cold. Further, combinations of mechanical and temperature feedback can be employed using the module 42 in other situations, such as to indicate the use of the catheter 18 in a long burn with poor contact. Additionally, in order to provide haptic feedback in the form of warnings to the user, in one exemplary non-limiting embodiment the module 42 can employ transducer 44-46 or other temperature-variable element that can incrementally heated to indicate to the user the growing risk of burn through, and the extended duration of the ablation sequence can thus be felt by the user through the module 42.

As discussed above, the haptic feedback module 42 may be pre-programmed or a user may optionally make selections to experience augmented or enhanced feedback in the form of force, or temperature, vibration or other forms of feedback, not necessarily corresponding, for example, to forces experienced by the user during manual catheter operation, such as, pressure, elasticity, angle of attack, texture, oscillations caused by cardiac or respiratory motion, and others. For example, a signal from a temperature sensor 35 on tip 33 during ablation may be converted to a force or vibration signal to alert a user of, for example, tissue overheating. Also, texture could be obtained from such information as a high frequency signal on the force sensor 35 while in contact with tissue.

Also, the haptic feedback provided to the user through the operation of the transducers 44-46 in zones 47 can be controlled, lessened or augmented in order to convey additional information on the sensed conditions being transmitted via the haptic feedback. For example, the amount of force feedback from the module 42 may be modulated, such that the amount of force is proportional or scaled/amplified to the signal being provided by the sensor 35. Further, in the case of haptic feedback form the module 42 indicative of temperature, module 42 may be heated or cooled as the temperature at a catheter electrode tip 33 or other contact area heats or cools between predetermined temperature thresholds. The temperature of module 42 may be scaled up or down based on specific user requirements and tolerance factors. For example, in the case of a cryocatheter 18 for which the catheter tip 33 temperature reaches liquid nitrogen temperatures, the temperature variation provided by the module 42 may be scaled to safe levels detectable and tolerable by a user, such as disclosed in U.S. Pat. No. 8,390,438, entitled Robotic Catheter System Including Haptic Feedback, which is expressly incorporated herein by reference for all purposes.

With the haptic feedback module 42, there are a number of technical advantages provided to the user of a catheter 18 in an interventional procedure, including, but not limited to:
  providing additional information to the user in the form of physical interactions/haptic feedback supplementing the user interface(s) or display 24;
  providing reinforcement to warnings from other components of the system 16;
  providing different types of messages via the patterns or sequences of operation; and
  providing an amplification of the point of contact between the patient and the physician.

In addition to the technical advantages, certain commercial advantages of the module 42 include, but are not limited to:
  providing a more immersive experience in the procedure enhancing situational awareness;
  providing unique/programmable user-catheter relationships with regard to the system 16 help improve procedure outcomes by providing a more implicit sense based approach to observing the delivery process; and
  reducing complications by providing the user with additional information concerning the duration of the procedure and risk of perforation.

Figure 4:
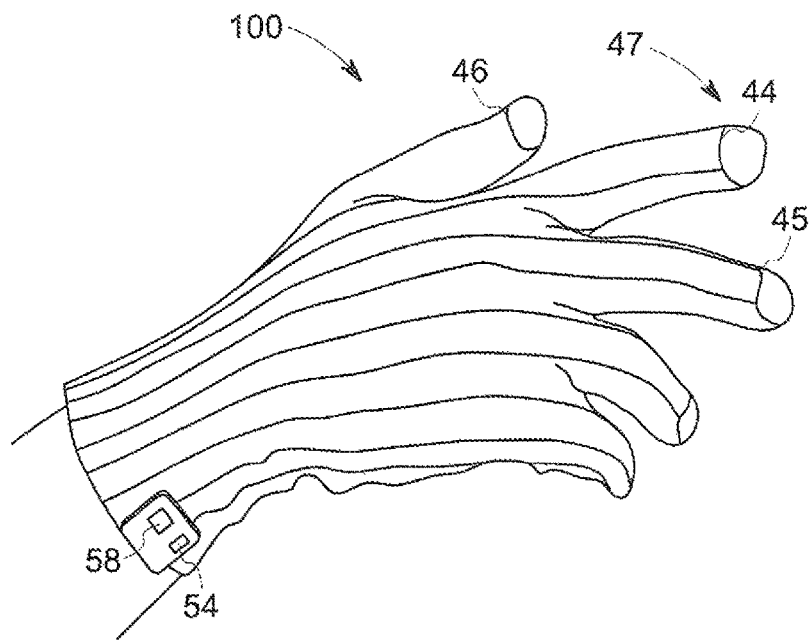
FIG. 4 is an isometric view of haptic feedback interface module according to another exemplary non-limiting embodiment of the invention.

Looking now at FIG. 4, in another exemplary non-limiting embodiment the module 42 takes the form of a glove 100 that is worn over the hand of the user. The glove 100 includes the transducers 44-46, processing unit 58 and power source 57 as are present in housing 48 and the wireless transceiver 54 to receive the patterns/sequences for operation of the transducers 44-46, optionally in zones 47, from the system 16. When worn, the transducers 44-46 in zones 47 are activated to provide the haptic feedback to the wearer in the manner described above with respect to the module 42.

Figure 5:
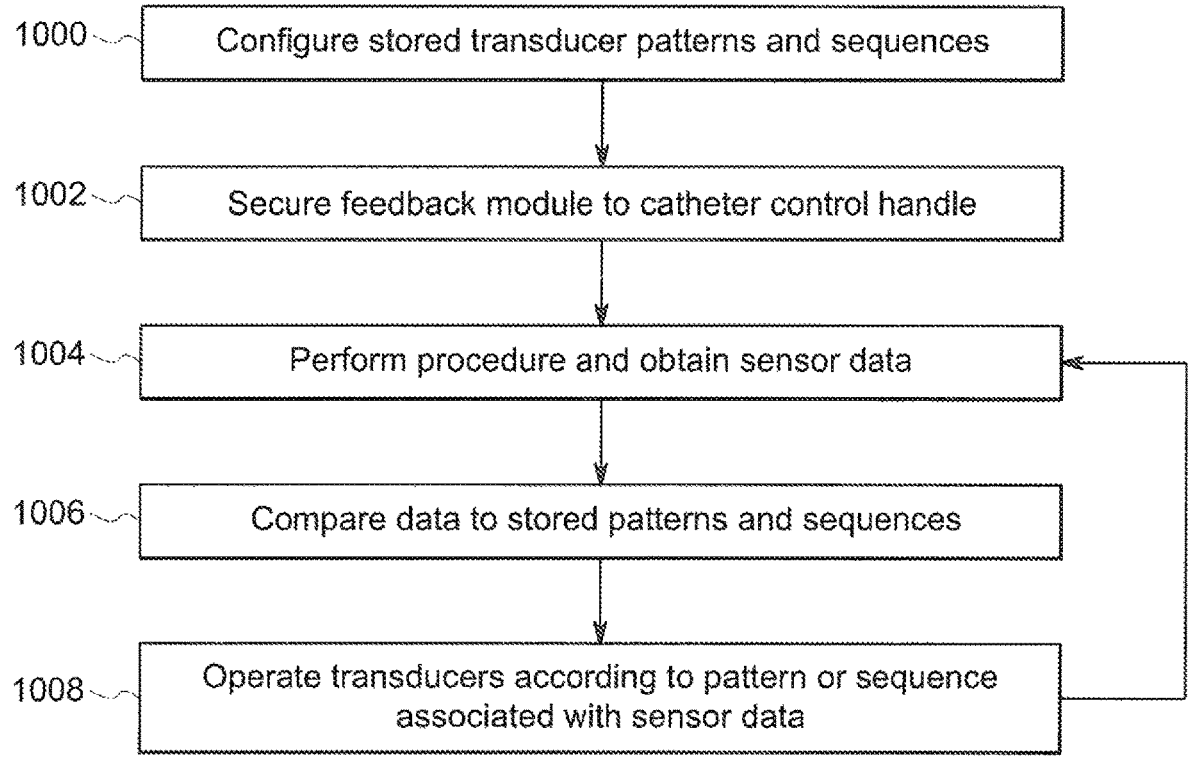
FIG. 5 is a schematic of a method of operation of the haptic feedback interface module according to an exemplary non-limiting embodiment of the invention.

In one exemplary non-limiting embodiment of a method of operation of the haptic feedback module 42, shown in FIG. 5, in block 1000 the operation of the interface control 42 is configured by accessing the pre-programmed patterns or sequences provided for the procedure to be performed using the catheter 18 in conjunction with the module 42. The pre-programmed patterns and sequences can be altered if desired, such as by using the interface 26 for the system 16 in order to configure the activation of the module 42 as desired. Once configured, in block 1002 the module 42 is positioned on the catheter handle 36, or in the case of the glove 100 is positioned on the hand of the wearer. Once positioned, in block 1004 the user proceeds to perform the procedure using the module 42 such that data from sensors 35 is received by the system 16. This data is compared in block 1006 with the various patterns and sequences stored in the system 16 or directly in storage media within the module 42 to locate the associated pattern for the operation of the transducers 44-46 on the module 42 or glove 100. Once located, in block 1008 the processing unit 58, optionally under the direction of the system 16, operates one or more of the transducers 44-46, such as those transducers 44-46 in predetermined zones 47 as identified by the associated pattern, in the associated pattern or sequence to provide the haptic feedback to the user to tactilely indicate the data from the sensors 35 received by the system 16 to the user. As stated previously, this feedback can be indicative of the data from the catheter 18, as a result or confirmation of various steps in the particular procedure being performed, interface actions or can be triggered from suitable computer algorithms within the system 16 relative to warning or feedback sequences based on data from the sensors 35. Further, after the transducers 44-46 have been operated to provide the haptic feedback to the user via the module 42,100, the system 16 can return to block 1004 to obtain additional sensor data to provide further haptic feedback as the procedure proceeds. The cycle time for the different feedback provided by the module 42,100 can be selected as desired to effectively provide the haptic feedback to the user in a timely and relatively real-time manner.

With the deployment of the haptic feedback module 42 on the control handle 36 or on the hand of the wearer, i.e., the glove 100, in contact with the control handle 36, the haptic feedback module 42,100 provides the physician with the ability to receive implicit direction/guidance from the computer system 16 during the procedure. Through the feedback module 42,100, the user is in direct, i.e., non-robotic, and constant touch with the procedure and can interpret the feedback to provide additional guidance either in navigation, tissue contact, or confirmation of the procedural steps to be performed.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A haptic feedback module for a catheter control handle utilized in a non-robotic interventional medical procedure, the haptic feedback module comprising:
 a housing configured to be releasably secured to an exterior of a control handle;
 a cable connected to and extending outwardly from the housing for connection to the handle or a computer system; and
  a number of transducers disposed at least partially within the housing, wherein the number of transducers are operable to provide haptic feedback in response to signals from the computer system.

2. The haptic feedback module of claim 1 further comprising a wireless transceiver disposed within the housing and configured to wirelessly connect the transducers to the computer system.

3. The haptic feedback module of claim 1 further comprising a cable extending outwardly from the housing and configured to operably connect the transducers to the computer system.

4. The haptic feedback module of claim 3 wherein the cable is configured to be directly connected to the computer system.

5. The haptic feedback module of claim 3 wherein the cable is configured to be directly connected to the catheter control handle.

6. The haptic feedback module of claim 3 wherein the housing comprises:
 an upper portion on which the transducers are disposed; and
 a number of lower portions extending outwardly from the upper portion, wherein the lower portions include an engagement structure thereon configured to engage the catheter control handle.

7. The haptic feedback module of claim 1 further comprising:
 a processing unit operably connected to the transducers; and
 electronic storage media operably connected to the processing unit and configured to store patterns or sequences of operation of the transducers corresponding to one or more of sensor data, steps in a medical interventional procedure, interface actions or sensor warnings.

8. The haptic feedback module of claim 1 wherein the housing comprises a glove.

9. A catheter control handle comprising:
 a housing;
 a shaft extending outwardly from the housing, the shaft terminating in a tip including at least one sensor;
 a conductor extending outwardly from the housing and configured to be connected to an computer system to supply sensor data thereto;
 a control device disposed on the housing and connected to the shaft to control the shaft; and
 the haptic feedback module of claim 1.

10. A catheter control handle comprising:
 a housing;
 a shaft extending outwardly from the housing, the shaft terminating in a tip including at least one sensor;
 a conductor extending outwardly from the housing and configured to be connected to a computer system to supply sensor data thereto;
 a control device disposed on the housing and connected to the shaft to control the shaft; and
 a haptic feedback module releasably disposed on an exterior of the housing, the haptic feedback module configured to be connected to a computer system to control the operation of the haptic feedback module in response to signals from the computer system relating to sensor data, steps in a non-robotic medical interventional procedure, interface actions or sensor warnings wherein the haptic feedback module includes a cable connected to and extending outwardly from the housing for connection to the handle or the computer system.

11. The control handle of claim 10 wherein the haptic feedback module comprises a number of transducers disposed adjacent the control device and configured to be operably connected to the computer system to control the operation of the transducers.

12. The control handle of claim 11 wherein the haptic feedback module comprises a glove.

13. The control handle of claim 11 wherein the haptic feedback module comprises:
 a. a processing unit operably connected to the transducers; and
 b. electronic storage media operably connected to the processing unit and configured to store patterns or sequences of operation of the transducers corresponding to one or more of sensor data, steps in a medical interventional procedure, interface actions or sensor warnings.

14. The control handle of claim 11 wherein the haptic feedback module is operably connected to the conductor.

15. The haptic feedback module of claim 1 wherein the number of transducers are disposed at least partially on an exterior of the housing.

* * * * *

UNITED STATES PATENT AND TRADEMARK OFFICE
CERTIFICATE OF CORRECTION

PATENT NO. : 10,610,318 B2
APPLICATION NO. : 15/218640
DATED : April 7, 2020
INVENTOR(S) : Adrian F. Warner et al.

It is certified that error appears in the above-identified patent and that said Letters Patent is hereby corrected as shown below:

In the Claims

Claim 9, Column 12, Line 4, delete "an" and substitute therefor -- a --;

Claim 10, Column 12, Line 24, after "warnings" insert -- , --.

Signed and Sealed this
Sixteenth Day of June, 2020

Andrei Iancu
*Director of the United States Patent and Trademark Office*